United States Patent [19]

Vanderpool

[11] Patent Number: 4,605,538

[45] Date of Patent: Aug. 12, 1986

[54] PRODUCTION OF PURE MOLYBDENUM

[75] Inventor: Clarence D. Vanderpool, Towanda, Pa.

[73] Assignee: GTE Products Corporation, Stamford, Conn.

[21] Appl. No.: 768,387

[22] Filed: Aug. 22, 1985

[51] Int. Cl.$^4$ ............................................. C01G 39/00
[52] U.S. Cl. ....................................... 423/55; 423/58; 546/2
[58] Field of Search ..................... 423/55, 58; 544/181; 546/2

[56] References Cited

U.S. PATENT DOCUMENTS 4,266,051 5/1981 Kroenke ............................... 544/181
4,355,161 10/1982 Johnson et al. ...................... 544/181

Primary Examiner—H. T. Carter
Attorney, Agent, or Firm—Donald R. Castle; L. Rita Quatrini

[57] ABSTRACT

A process is disclosed for producing pure molybdenum which involves contacting a molybdate solution with a true liquid alkaloid in an amount sufficient to form an alkaloid-molybdenum compound with essentially all of the molybdenum. The resulting alkaloid-treated solution is adjusted to a pH of from about 2 to 4 to form a precipitate consisting essentially of the compound and a mother liquor. The precipitate is then separated from the mother liquor and dissolved in ammonium hydroxide to form a two phase system consisting essentially of an alkaloid phase and a molybdenum phase followed by separation of the two phases. A pure ammonium molybdate compound is then crystallized from the molybdenum phase.

4 Claims, No Drawings

PRODUCTION OF PURE MOLYBDENUM

BACKGROUND OF THE INVENTION

This invention relates to a process for producing pure molybdenum. More particularly it relates to a process for producing pure molybdenum by formation and precipitation of an alkaloid-molybdenum compound.

Impure molybdenum, particularly in the form of molybdenum trioxide can be converted to pure molybdenum trioxide by sublimation. However, sublimation is a relatively inefficient method of purification since efficiencies are only about 60% to about 70%. The reason for this inefficiency is that molybdenum trioxide sublimes efficiently at temperatures approaching its melting point (about 750° C.). However, if the molybdenum trioxide melts, it contaminates the furnace. At lower temperatures the molybdenum trioxide sublimes very slowly.

Other methods for producing pure molybdenum from impure molybdenum trioxide are (1) by leaching with nitric acid which usually does not remove potassium and lowers the yield; and (2) firing followed by washing with water or nitric acid which also results in relatively low yields.

SUMMARY OF THE INVENTION

In accordance with one aspect of this invention, there is provided a process for producing pure molybdenum which involves contacting a molybdate solution with a true liquid alkaloid in an amount sufficient to form an alkaloid-molybdenum compound with essentially all of the molybdenum. The resulting alkaloid-treated solution is adjusted to a pH of from about 2 to 4 to form a precipitate consisting essentially of the alkaloid-molybdenum compound and a mother liquor. The precipitate is then separated from the mother liquor and dissolved in ammonium hydroxide to form a two phase system consisting essentially of an alkaloid phase and a molybdenum phase followed by separation of the two phases. A pure compound is then crystallized from the molybdenum phase.

DETAILED DESCRIPTION OF THE INVENTION

For a better understanding of the present invention, together with other and further objects, advantages, and capabilities thereof, reference is made to the following disclosure and appended claims in connection with the above description of some of the aspects of the invention.

The source of molybdenum used in the practice of this invention is, in general, any impure source which can be solubilized. One preferred source is relatively impure molybdenum trioxide which can be dissolved in ammonium hydroxide, sodium hydroxide, and the like to produce a molybdate solution. Especially preferred is ammonium hydroxide at a pH of preferably from about 9.0 to about 10.0 which results in an ammoniacal molybdate solution. The solution can be treated such as by filtering to remove any insoluble impurities such as iron. It is preferred that the pH of the solution be from about 9 to 10 to insure that the alkaloid will dissolve when it is added.

The solution is then contacted with a true liquid alkaloid as opposed to protoalkaloids and pseudoalkaloids. The amount of the alkaloid is sufficient to form an alkaloid-molybdenum compound containing essentially all of the molybdenum values. The preferred alkaloids are nicotine and conine with nicotine being especially preferred. When nicotine is used, the amount is generally about 0.1 moles of nicotine to about 0.5 moles of $MoO_3$.

The pH of the resulting alkaloid-treated solution is adjusted to from about 2 to 4 preferably with hydrochloric acid to form a precipitate consisting essentially of the alkaloid-molybdenum compound and a mother liquor. Essentually all of the impurities such as sodium and potassium remain in the mother liquor.

The precipitate is then separated from the mother liquor by any standard technique such as filtration.

The precipitate can be washed with water, preferably hot water to remove any remaining soluble impurities.

The precipitate is then dissolved in ammonium hydroxide which is preferably at a pH of from about 9 to 10 to form a two phase system consisting essentially of an alkaloid phase and an ammoniacal molybdenum phase. The liquid alkaloid phase is lighter than the liquid molybdenum phase and rises to the top of the containing vessel, and the two phases are separated by any conventional method for separating two liquid phases. The alkaloid can be reused, which has an economical advantage.

A pure molybdate compound is then crystallized from the ammoniacal molybdenum phase by standard techniques such as by evaporation to dryness to form ammonium paramolybdate.

The ammonium molybdate compound can be reduced to molybdenum metal by well known methods.

If further purification is desired, the precipitate of the alkaloid-molybdenum compound before being further processed can be dissolved in ammonium hydroxide and the pH adjusted to from about 2 to 4 preferably with hydrochloric acid to reprecipitate the alkaloid-molybdenum compound. The precipitate is then separated from the resulting mother liquor and water washed. The dissolution in ammonium hydroxide, pH adjustment, precipitation and washing steps can be carried out any number of times until the desired purity of the molybdenum is attained.

To more fully illustrate this invention, the following nonlimiting example is presented. All parts, portions, and percentages are on a weight basis unless otherwise stated.

EXAMPLE

About 100 parts of impure molybdenum trioxide are slurried in about 40 parts of water and enough reagent grade ammonium hydroxide to completely dissolve the molybdenum trioxide. The resulting solution is filtered to remove the hydroxides of iron. About 16 parts of nicotine are added to the filtered solution and the pH is adjusted to about 2.0 with hydrochloric acid. The resulting white precipitate of nicotine-molybdenum is filtered off and washed with about 1000 parts of hot water. The nicotine-molybdenum precipitate is again dissolved in ammonium hydroxide, reslurried, and the pH of the nicotine-treated solution is adjusted to about 2.0 with hydrochloric acid to reprecipitate the nicotine-molybdenum compound which is then filtered off and washed with about 1000 parts of hot water. The resulting nicotine-molybdenum precipitate is again dissolved in ammonium hydroxide. The nicotine phase comes to the top of the reaction vessel and is separated for reuse. The molybdenum containing phase is then evaporated to dryness to produce ammonium paramolybdate crystals. The ammonium paramolybdate is reduced to molybdenum powder.

The following is an analysis of the molybdenum produced by the purification process of this invention and an analysis of a molybdenum metal produced by another process which is used as a control sample.

| Control | AL | Ca | Cr | Cu | Fe | Mg | ppm Mn | Ni | Pb | Si | Sn | Na | K |
|---|---|---|---|---|---|---|---|---|---|---|---|---|---|
| Mo | 10 | 6 | 15 | 5 | 10 | 7 | 7 | 7 | 7 | 50 | 10 | 5 | 30 |
| Mo this Invention | <5 | <1 | <3 | <3 | <3 | <1 | 3 | 2.1 | <4 | <15 | <10 | <5 | <10 |

It can be seen that the molybdenum produced from ammonium molybdate purified by the process of this invention is purer than the control sample.

While there has been shown and described what are at present considered the preferred embodiments of the invention, it will be obvious to those skilled in the art that various changes and modifications may be made therein without departing from the scope of the invention as defined by the appended claims.

What is claimed is:

1. A process for producing pure molybdenum, said process comprising:
    (a) contacting a molybdate solution with a true liquid alkaloid that is capable of dissolving in an aqueous solution of molybdenum values when said solution is at a pH of from about 9 to 10 with the amount of the alkaloid being sufficient to form an alkaloid-molybdenum compound with essentially all of the molybdenum;
    (b) adjusting the resulting alkaloid-treated solution to a pH of from aout 2 to about 4 to form a precipitate consisting essentially of said compound and a mother liquor;
    (c) separating said precipitate from said mother liquor;
    (d) dissolving said precipitate in ammonium hydroxide to form a two phase system consisting essentially of an alkaloid phase and a molybdenum phase;
    (e) separating said alkaloid phase from said molybdenum phase; and
    (f) crystallizing a pure ammonium molybdate compound from said molybdenum phase.

2. A process of claim 1 wherein said alkaloid is selected from the group consisting of nicotine and conine.

3. A process of claim 2 wherein said alkaloid is nicotine.

4. A process of claim 1 wherein after the precipitation of said alkaloid molybdenum compound and separation of the precipitate from said mother liquor, the precipitate is dissolved in ammonium hydroxide, the pH is adjusted to from about 2 to about 4 to reprecipitate said alkaloid-molybdenum compound, and the reprecipitated compound is separated from the resulting mother liquor, the dissolution and pH adjustment steps being carried out one or more times.

* * * * *